United States Patent [19]

Pearse et al.

[11] Patent Number: 5,446,383
[45] Date of Patent: Aug. 29, 1995

[54] METHOD AND APPARATUS FOR DETECTING MAGNETIC ANOMALIES IN A DIFFERENTIAL TRANSFORMER CORE

[75] Inventors: James N. Pearse, Dix Hills; Bernard Gershen, Centerport, both of N.Y.

[73] Assignee: Leviton Manufacturing Co., Inc., Little Neck, N.Y.

[21] Appl. No.: 212,675

[22] Filed: Mar. 11, 1994

Related U.S. Application Data

[63] Continuation of Ser. No. 975,155, Nov. 12, 1992, abandoned, which is a continuation of Ser. No. 780,573, Oct. 22, 1991, abandoned, which is a continuation of Ser. No. 667,912, Mar. 12, 1991, abandoned, which is a continuation of Ser. No. 557,340, Jul. 25, 1990, abandoned, which is a continuation of Ser. No. 382,208, Jul. 24, 1989, abandoned.

[51] Int. Cl.⁶ ............... G01R 33/12; G01N 27/82
[52] U.S. Cl. ................... 324/240; 324/232; 324/239; 324/262
[58] Field of Search .............. 324/211, 222, 223, 232, 324/239, 240, 241, 262, 377, 545

[56] References Cited

U.S. PATENT DOCUMENTS

| | | | |
|---|---|---|---|
| 1,373,383 | 3/1921 | Couch | 324/545 |
| 2,134,539 | 10/1938 | Thal | 324/223 |
| 2,331,418 | 10/1943 | Nolde | 324/239 X |
| 2,904,745 | 9/1959 | Bugg | 324/239 |
| 2,924,773 | 2/1960 | Lykke | 324/239 X |
| 2,999,981 | 9/1961 | Probert | 324/239 |
| 3,068,380 | 12/1962 | Lamoreaux | 324/211 X |
| 3,492,566 | 1/1970 | Gross | 324/377 X |

FOREIGN PATENT DOCUMENTS

| | | | |
|---|---|---|---|
| 548915 | 4/1932 | Germany | 324/545 |
| 618050 | 2/1949 | United Kingdom | 324/545 |
| 0849056 | 7/1981 | U.S.S.R. | 324/240 |
| 928258 | 5/1982 | U.S.S.R. | 324/545 |

*Primary Examiner*—Gerard R. Strecker
*Attorney, Agent, or Firm*—Paul J. Sutton

[57] ABSTRACT

A device for and method of testing toroidal magnetic cores for magnetic anomalies which prevent uniform performance of the cores. The core is positioned on a drive device which can rotate the core through 360°. The core passes through an input winding which receives the test signal and an output winding coupled to a display device which shows the presence or absence of such magnetic anomalies.

16 Claims, 14 Drawing Sheets

MIN. POSITION 5,446,383

METHOD AND APPARATUS FOR DETECTING MAGNETIC ANOMALIES IN A DIFFERENTIAL TRANSFORMER CORE

The instant application Ser. No. 08/212,675, filed Mar. 11, 1994 is a continuation of application Ser. No. 07/975,155, filed Nov. 12, 1992, now abandoned, which is a continuation of application Ser. No. 07/780,573, filed Oct. 22, 1991 and now abandoned, which in turn is a continuation of application Ser. No. 07/667,912, filed Mar. 12, 1991, and which is now abandoned, which in turn is a continuation of application Ser. No. 07/557,340, filed Jul. 25, 1990 and which is now abandoned, and which in turn is a continuation of application Ser. No. 07/382,208, filed Jul. 24, 1989 and now abandoned.

BACKGROUND OF THE INVENTION

The present invention relates generally to a method and apparatus for evaluating magnetic cores, and, more specifically to a method and apparatus for detecting magnetic anomalies in the magnetic cores used for the differential transformers employed in ground fault circuit interrupters.

A differential transformer has an opening in the middle through which the wires being monitored thread through. These wires are arranged so that the outgoing current through one wire produces a magnetic field in the differential transformer which is cancelled by the magnetic field set up by the incoming current through the other wire. If both currents are equal, the magnetic flux in the differential transformer is zero. If the two currents are not exactly equal, a net magnetic flux is established in the differential transformer which produces a voltage in a sense winding wound around the differential transformer itself, and which voltage then constitutes a signal to trip a ground fault circuit interrupter at a pre-established value of difference current.

It is well known that the magnetic cores used for the differential transformers employed in ground fault circuit interrupters, such as those marketed by the assignee of the present invention, must be homogeneous and of a high permeability. In particular, a departure from homogeneity results in the differential transformer being sensitive to magnetic fields other than those caused by current in the wires passing through the center of the toroidal core used in the transformer, thus rendering the finished ground fault circuit interrupter unacceptable. These stray magnetic fields may be produced by the current in the wires threading the center of the toroidal core from points on the wire distant from the center of the core, and maybe at an angle to the core caused by bending of the wires themselves. Ordinarily, this type of defect is not detected until the finished product is assembled and tested.

"Load Shift" is defined as a change in trip current in a ground fault circuit interrupter from no load to full load conditions. Depending upon whether the trip current (fault) is introduced between line phase to load neutral, or load phase to line neutral, the phenomenon will add to, or subtract from, in a generally symmetrical manner, the trip current measured at no load. In the first case, the neutral current will be larger than the phase current at the point where the two wires thread the differential transformer, while in the second case the phase current will be larger than the neutral current at that point.

Thus, a product which should trip between 4 and 6 milliamperes may measure between that specification at no load and be out of that specification at some value of load current, with the most common measurement at the maximum rating of 20 amperes. In some cases, the device will trip with no fault current applied during a 120 amp surge current test, meant to simulate motor inrush current.

It is thus clear that what is needed is a reliable and accurate way of evaluating the component cores prior to the labor intensive and expensive manufacturing steps involved in the wiring and assembly of the cores into the finished ground fault circuit interrupter product. Prior to the present invention it is believed that said need has gone unfulfilled.

Accordingly, it is a general object of the present invention to provide a method and apparatus for evaluating magnetic cores.

It is a specific object of the present invention to overcome the aforementioned difficulties and to fulfill the long felt needs by providing a method and apparatus for detecting magnetic anomalies in magnetic cores of the type used for the differential transformers employed in ground fault circuit interrupters.

It is a further object of the invention to provide a method and apparatus for evaluating the permeability and homogeneity of magnetic cores of the type used for the differential transformers employed in ground fault circuit interrupters.

Other objects of the invention will be apparent in the following detailed description and practice of the invention.

SUMMARY OF THE INVENTION

The foregoing and other objects and advantages which will be apparent in the following detailed description of the preferred embodiment, or in the practice of the invention, are achieved by the invention disclosed herein, which generally may be characterized as a method and apparatus for detecting magnetic anomalies in transformer cores, wherein a magnetic field having a predetermined flux distribution is created in the vicinity of the core; and the AC voltage induced in a sensing winding placed about the core as a result thereof is observed as the core is rotated 360° about its axis.

BRIEF DESCRIPTION OF THE DRAWINGS

Serving to illustrate exemplary embodiments of the invention are the drawings of which.

DESCRIPTION OF THE PREFERRED EMBODIMENT

Figure 1:
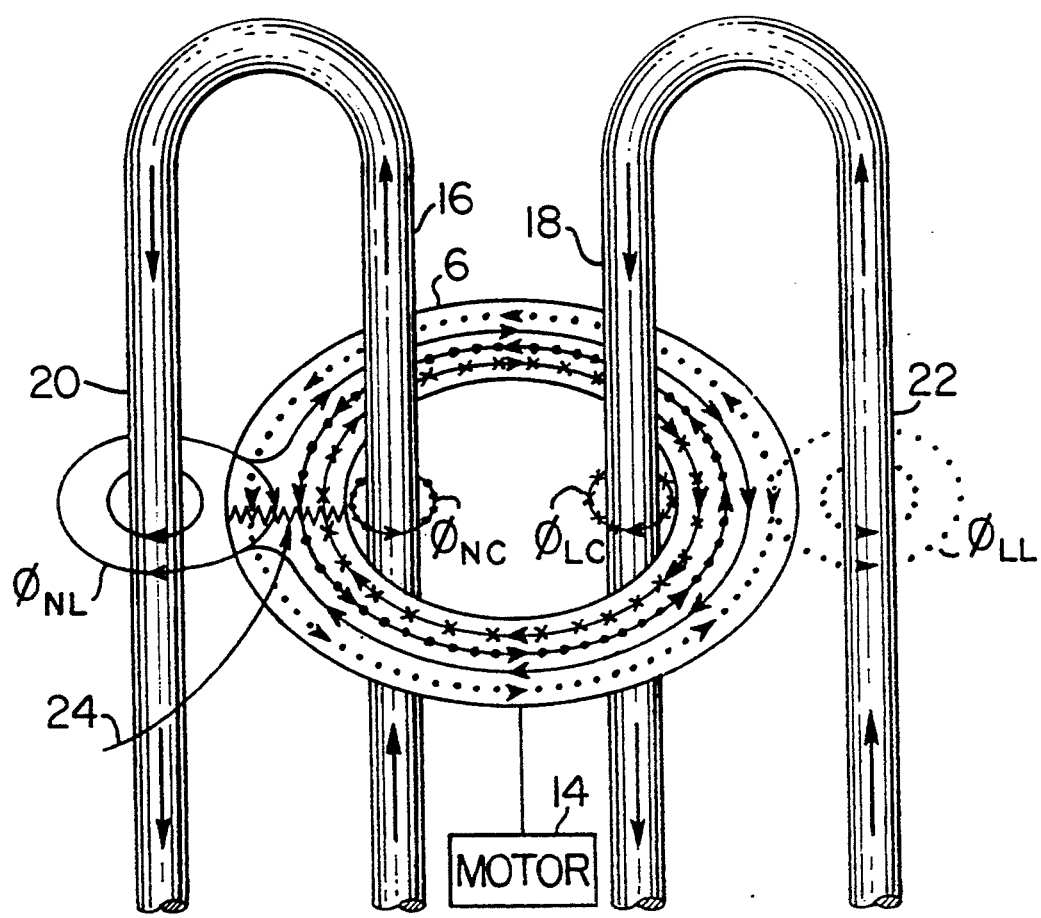
FIG. 1 illustrates the mechanism by which a magnetic anomaly in the core can result in the load shift phenomenon.

Load shift can be caused by lack of symmetry between the line and neutral lead wires, and particularly by a non-uniformly wound differential transformer. We also know that it can be reduced by magnetic shielding of the differential transformer, and by demagnetizing the transformer. However, the beneficial effect of demagnetizing the transformer is lost because the same load shift performance reappears after surge testing Or DC shock. This latter phenomenon indicates magnetic anisotropy (remnant flux).

It will now be explained how, in a perfectly symmetrical construction, with a uniformly wound differential transformer, load shift can occur due to lack of uniformity or homogeneity in the magnetic material of the differential transformer itself, even in a high permeability core.

There are a number of possible causes for this transformer core non-uniformity, which we call magnetic anomalies, such as anisotropic material, remnant flux (square loop material), localized damage, material impurities, magnetostriction, improper annealing procedures and non-uniform permeability. In one particular case, we have determined the phenomenon to be localized damage caused by mechanical deformation of the individual stamped rings during the casing operation.

There are always questions dealing with the basic material, which is manufactured in coil form. Each coil is carefully inspected for magnetic properties, with sample rings stamped from the beginning and end. These sample rings are annealed to the proper state and checked for permeability, resistivity, and proper BH loop.

Localized material impurities could produce an occasional bad core, but not at a significant percentage. These defects would be obvious during metallurgical examination.

Improper annealing procedures would also be easy to determine. For example, at one manufacturer's facility, 3,000 rings are placed on a rod, and a series of rods are passed through their annealing furnace. At another manufacturer's facility, rings are placed in trays, approximately 15,000 per tray, and annealed in a similar fashion. Checks are made from each rod and/or tray with respect to permeability and BH loop.

Thus, defects in the basic material or in the annealing process are easily controlled. Anisotropic material, which would show a preferred direction of magnetization, would also be easy to determine, as would remnant flux and improper BH loop, as all are related.

However, localized damage could produce anisotropic behavior, low permeability, and remnant flux at the point of damage. In fact, no "damage" need occur, only mechanical strain. This phenomenon is known as magnetostriction. This type of defect could occur on a significant percentage of cores, if not controlled.

Basically, magnetostriction is defined as the following: 1. deformation in magnetic material as a result of a magnetic field; or 2. change in magnetic properties as a result of mechanical strain.

Magnetostriction is generally proportional to the square of the flux density in a relationship as follows:

$$\frac{\Delta L}{L} = KB^2$$

Where K is a constant
B is flux density
$\Delta L$ is the change in some dimension, L, in a direction to reduce the reluctance of the field, B.

In this particular case, a strain in the differentially transformer rings produces a localized area of lower permeability. This localized area will generally be anisotropic, magnetically "hard, " and show remnant flux.

This localized damage can be caused by a variety of mechanical effects such as burrs, particulates between individual rings, improper case design, improper (high) casing pressure, improper design or assembly or case lid, etc.

The mechanism by which a magnetic anomaly in the core itself can result in a voltage on a uniformly wound toroid (differential transformer) of sufficient value to cause the load shift phenomenon can be understood by reference to FIG. 1. In this case, the permeability of the basic core material at the site of the magnetic anomaly is much lower than the permeability at other undamaged sections of the core.

The effect of this lower permeability at the site of the magnetic anomaly is twofold:

1. The flux ($\phi_{NC}$ and $\phi_{LC}$) produced by the current in the wires 16 receiving current on the neutral line to be applied to the load and 18 to which line current from the load is applied threading the interior of the core, although confined for the most part within the core, tends to "fringe" at the point of the anomaly, resulting in a lower voltage induced in the turns of the coil wound at that area as compared to the voltage at undamaged areas.

2. Of more importance is the flux ($\phi_{NL}$ and $\phi_{LL}$) produced by the current in the wires 20, (current returned to the AC voltage source in the neutral wire) and 22 (line current applied to AC voltage line by the AC voltage source) external to the core ($\phi_{NL}$ and $\phi_{LL}$). For example, $\phi_{NL}$ travels for the most part through air surrounding the neutral wire 20, and partially through a section of the toroidal core 6. When it enters the core 6, it sees a relatively high permeability path travelling completely around the core 6 and a relatively low permeability path through the magnetic anomaly 24, so it will essentially divide in the ratio of the permeability at that point, with the major portion of the flux taking the longer path. For $\phi_{LL}$ the reverse is true and this flux will take the shorter path because it has the highest permeability. Hence, there will be a much higher voltage induced in phase with the flux produced by the line current as opposed to the voltage in phase with the flux produced by the neutral current. This is in spite of the fact that the construction may be perfectly symmetric and the differential transformer core 6 wound in an absolutely uniform fashion.

It is also obvious that rotation of the transformer core 6 to position the magnetic anomaly on an axis between the line and neutral wires will tend to minimize the effect, and thus minimize a potential load shift in a completely assembled GFCI.

However, a change in permeability is not the only culprit. Along with lower permeability, a magnetic anomaly is also likely to be "hard" magnetically, and show a remnant flux, which will cause a different voltage for those turns in the area of the anomaly regardless of its position.

It is impossible to detect this condition using conventional techniques, as the conventional techniques give average readings for core permeability and other magnetic characteristics. Only an innovative approach with respect to the testing of these cores can uncover the existence of these defects.

Although these magnetic anomalies serve to decrease the average permeability of the cores, permeability by itself is not a measurement of whether or not a magnetic anomaly does exist. For example, a core with no magnetic anomaly and a permeability of 50,000 will be absolutely free of the load shift phenomenon. On the other hand, a core with an initial permeability of 80,000 which has been reduced to 50,000 as a result of magnetostriction (mechanical strain), will fail on our GFCI test program as a result of load shift. Nevertheless, both cased cores measured 50,000 on a permeability test after production, with one good and the other bad.

As with any mechanical strain, this can be subdivided into two further parts: 1. reversible strain, and 2. irreversible strain.

If an individual ring has been stressed beyond the elastic limit, the damage is irreversible and can be corrected by mechanically "bending back" and then re-annealing that ring to reinstate the proper magnetic properties. On the other hand, if the deflection has not passed the elastic limit, the core will return to its original magnetic properties upon removal of the force involved, and this constitutes a reversible behavior.

Basically, any cores which exhibit anisotropic behavior outside the limits of our specification are unusable in GFCI's, and must be considered defective, and not accepted for use. We have determined that one cause for this behavior is failure to perform the casing operation in such fashion as to minimize mechanical pressure on the individual cores, that can lead to the deformation of the cores of sufficient value to cause the load shift phenomenon.

Although the primary cause of the magnetic anomalies that produce the load shift phenomenon has been shown to be caused by "magnetostriction as a result of the casing operation, it is desirable to have a test fixture that will identify this behavior in the individual cores regardless of how it arises.

This fixture was developed, and can be best understood by reference to FIG. 2. An alternate fixture more suitable to a production type test fixture is shown in FIG. 3.

The basic operation of both fixtures with respect to the core itself is essentially the same. A magnetic field having a predetermined magnetic flux distribution is introduced on either side of the core 6 which is located centrally with a single turn search coil 30. The construction must be symmetrical in order to avoid the introduction of any extraneous noise voltage, and the flux on either side must be equal. In FIG. 2, this is accomplished by producing the flux by means of the same current through wire 26 directed on either side of the coil 30, and in FIG. 3, this is done by actual measurement at the pole faces on the "C" type laminations.

The single turn search coil 30 actually is connected to a high gain operational amplifier 32, designed to give a boost in voltage, which permits replication of the conditions used in the GFCI itself. The core 6 in test is then rotated for 360° about its axis and the voltage recorded on the output of the operational amplifier 32. The core under test may be supported and rotated using a drive system as shown in U.S. Pat. No. 409, 193 issued Aug. 20, 1889 to W. W. Griscom. The core would be supported on its inner surface by three rollers B, B and E (see FIG. 3 ) supported by a frame $C^1$ and driven by a centrally located axle A. The single turn search coil can be placed as desired about the core in the spaces between the rollers E and B, B and B or B and E. Other coils can also be placed about the core at the available spaces. Alternatively, the core could be driven between two rollers 6 and 7 through a core used as the loose belt 5 as shown in G. F. Evans, U.S. Pat. No. 453,630 issued Jun. 9, 1891. The single turn search coil could be placed about the core 5 wherever it will not be contacted by roller 7. Hardy, U.S. Pat. No. 462,433 issued Nov. 3, 1891 shows another three roller support and drive system where the core, in place of ring $C^2$, would be supported and driven by rollers $C^2$ which are in turn driven by roller $C^2$ mounted upon axle $A^2$. Again, the one turn search coil could be placed about the core at $C^2$ between the respective rollers $C^3$.

For a core 6 with no magnetic anomalies, the voltage will remain the same during the rotation of the core 6 itself. If the flux produced on either side is exactly the same, and the flux path has the same permeability within the core 6 (the core is located exactly at the center of the symmetrical fixture) then the voltage generated for a good core will be essentially zero. Where a magnetic anomaly exists, and assuming a single anomaly exists, there will be two maximum readings and two minimum readings as the core 6 is rotated 360°. The ratio of maximum to minimum voltage is an indication of the degree of susceptibility of the basic core to exhibit the load shift phenomenon, with a ratio of 1.5 to 1.0 established as a limiting specification with the operational amplifier uncorrected for white noise.

Figure 2A:
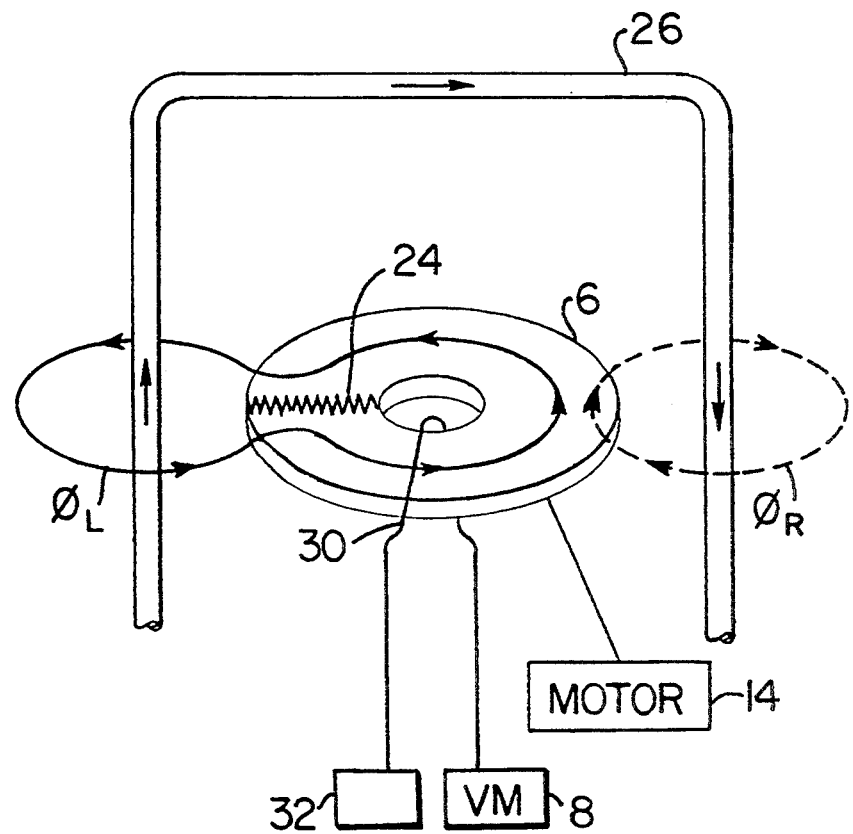
FIG. 2, made up of FIGS. 2a and 2b, illustrates one embodiment of a test fixture to evaluate load shift phenomenon.
Figure 2B:
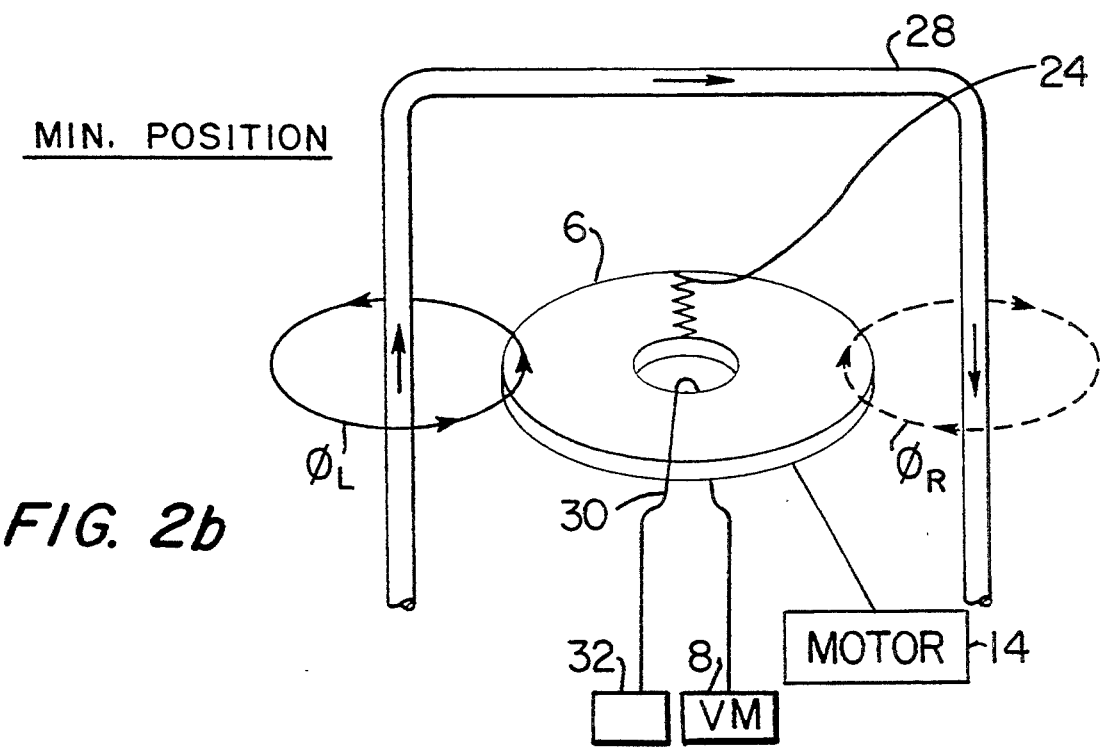
Figure 3:
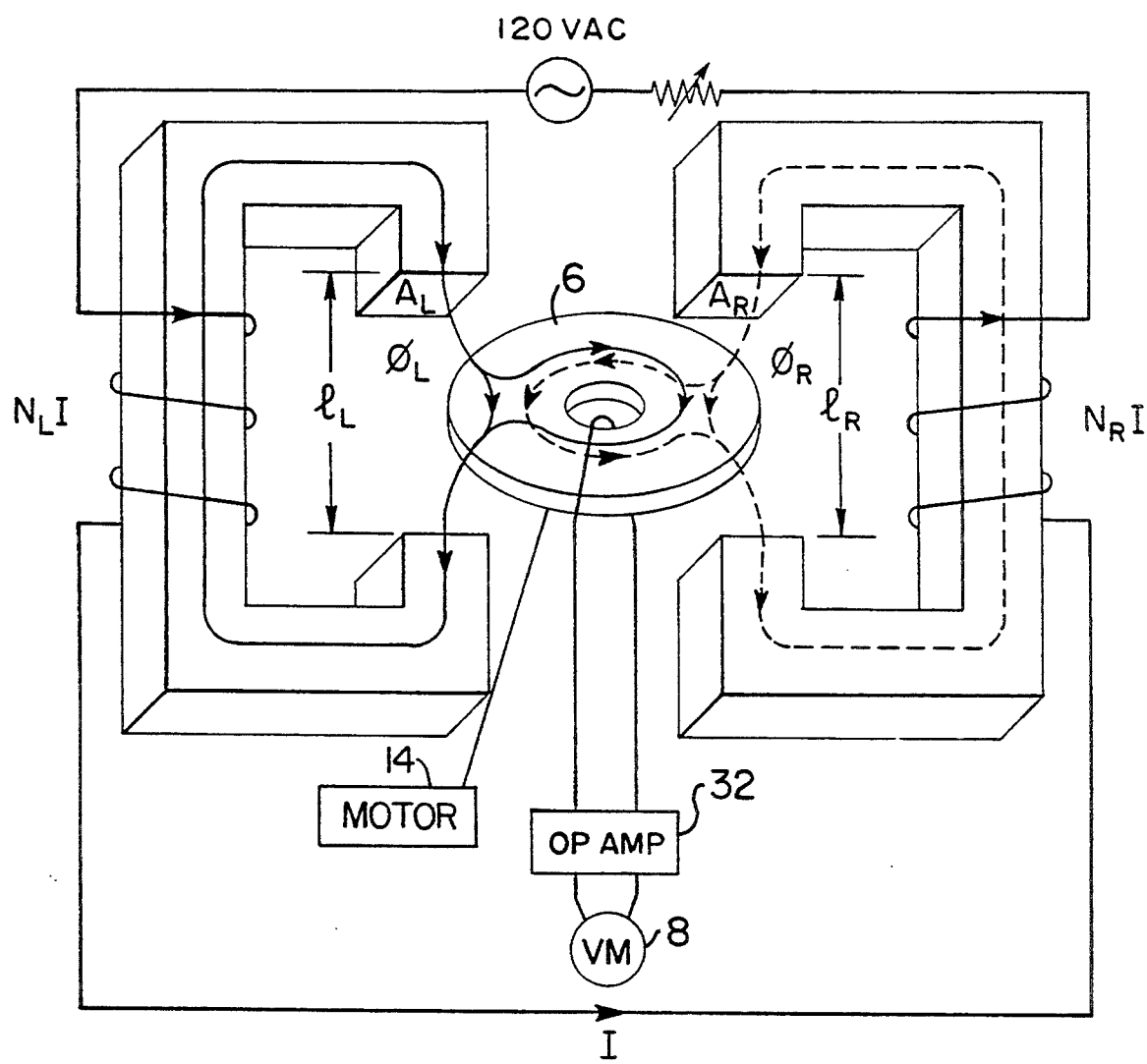
FIG. 3 illustrates an alternate embodiment of a test fixture to evaluate load shift phenomenon.

FIG. 2 shows the core 6 rotated in two specific positions where the flux produced by the current from one line (left side) dominating (max position see FIG. 2a), and in the second case with the fluxes produced by both lines essentially equal (min position see FIG. 2b) due to the location of the magnetic anomaly. It should be remembered that the anomaly is essentially an area of low permeability, and that the flux between tends to flow in the areas of high permeability since areas of low permeability resist the flow of flux.

As the core is rotated through 360°, the flux measured by the search coil will be in phase with the flux produced by the right hand source at one max position and in phase with the flux produced by the left hand source at the max position 180° opposite.

The important consideration is that regardless of the reason for the anomaly, this type of fixture serves to identify cores which have a magnetic anomaly that will exhibit the phenomenon known as load shift when assembled in a GFCI.

The key to the function of the test fixture is the introduction of magnetic flux from either side of the core and rotation of the core to then determine if anisotropic behavior occurs.

Typical test results are given in Table 1 below.

TABLE 1

| CORE NO | UNCORRECTED OF AMP | | | | OP AMP CORRECTED FOR NOISE | | | |
|---|---|---|---|---|---|---|---|---|
| | DEGAUSSED | | DC SHOCK | | DEGAUSED | | DC SHOCK | |
| | MIN | MAX | MIN | MAX | MIN | MAX | MIN | MAX |
| 1 | 1.6 | 2.8 | 1.5 | 4.1 | 0.7 | 2.5 | 0.7 | 3.8 |
| 2 | 1.4 | 3.5 | 1.7 | 5.3 | 0.6 | 2.9 | 0.8 | 5.2 |
| 3 | 1.4 | 3.3 | 1.5 | 5.7 | 0.6 | 2.8 | 0.6 | 5.3 |
| 4 | 1.4 | 2.5 | 1.6 | 4.2 | 0.6 | 2.5 | 0.7 | 4.1 |
| 5 | 1.4 | 2.4 | 1.5 | 4.4 | 0.6 | 1.8 | 0.6 | 4.3 |
| 6 | 1.5 | 1.7 | 1.6 | 1.9 | 0.7 | 1.1 | 0.8 | 1.1 |
| 7 | 1.5 | 1.6 | 1.6 | 1.7 | 0.7 | 0.8 | 0.7 | o.8 |
| 8 | 1.5 | 3.1 | 1.5 | 3.5 | 0.7 | 2.9 | 0.7 | 3.3 |
| 9 | 1.4 | 3.5 | 1.5 | 3.6 | 0.6 | 3.1 | 0.7 | 3.5 |
| 10 | 1.5 | 2.5 | 1.6 | 3.1 | 0.7 | 2.2 | 0.7 | 2.9 |

NOTES
1) cores 1–5 failed load shift test in GFCI
cores 6–10 passed load shift test in GFCI
2) cores 8–10 show tendency to fail load shift. They have a magnetic anomaly, probably an area of low permeability, but do not exhibit anisotropic behavior (remnant flux) as pronounced as cores 6–7 (see max values before and after DC shock)

Two sets of data are shown, with the operational amplifier corrected and uncorrected for white noise. Ten cores were tested, with five from "good" GFCI's and five from GFCI's with load shift failures.

Note the four columns marked min$^e$ which denote the minimum output voltage while rotating the cores. These readings are essentially the same for all cores which is to be expected. The only difference is the consistently lower reading for the case where the operational amplifier was corrected for white noise.

For "bad" cores, the maximum voltage reading is markedly higher than the minimum reading. In fact, cores 8, 9 and 10 from "good" GFCI's are really defective cores, and are actually marginal in performance in spite of having passed the load shift test. Only cores 6 and 7 are relatively free from defects.

Of particular interest is the performance comparison after demagnetization (degaussed) as opposed to the readings after application of a magnetizing field (DC shock). For good cores (6 and 7) there is no change. For bad cores (1–5, 8–10, there is a substantial change in the maximum voltage readings. This is proof of anisotropic behavior, showing a preferred direction of domain alignment and indicating remnant flux, all in a localized area of the cores.

Thus a substantial change in maximum voltage reading from demagnetized to magnetized condition is an additional indication of a magnetic anomaly and a tendency to fail when assembled in a GFCI when subjected to the load shift test. As explained earlier, the differential transformer turns in the area of the magnetic anomaly will produce a different voltage, due to this remnant flux, than the turns at undamaged areas of the transformer core.

Although these particular fixtures are successful in identifying cores with magnetic anomalies, other fixtures may serve to give the same results. The key factors for such fixtures are the following:

1. A source of flux that will proceed in a symmetrical pattern through the plane of the magnetic core.
2. A search coil located at a specific point or points of the magnetic core.
3. A volt meter or amplification means attached to this search coil with sufficient sensitivity to record the voltage produced by the flux in the core.
4. Means to rotate the core in a symmetrical fashion about its axis perpendicular to the plane of the core at least 180° but preferably 360°. These principles are exemplified in the typical fixtures shown in FIGS. 4 through 15, comprising four fixtures each shown in three different conditions.

Figure 4:
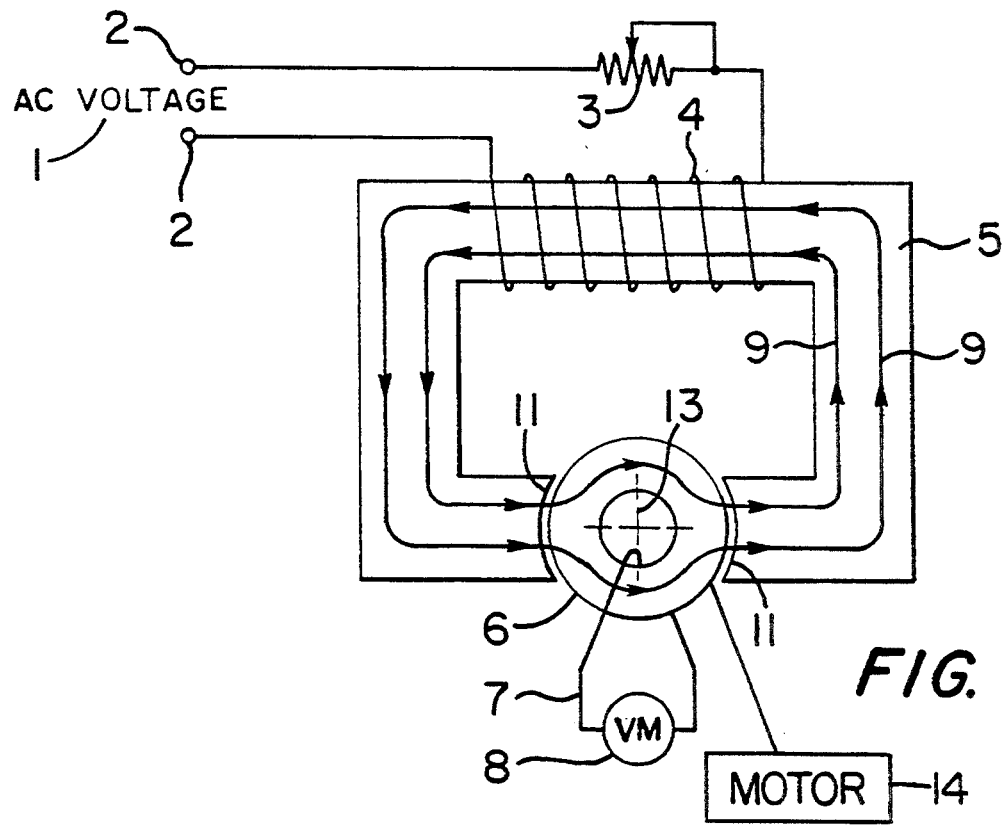
FIGS. 4–15 illustrate additional fixtures that may be utilized to identify cores with magnetic anomalies.
Figure 5:
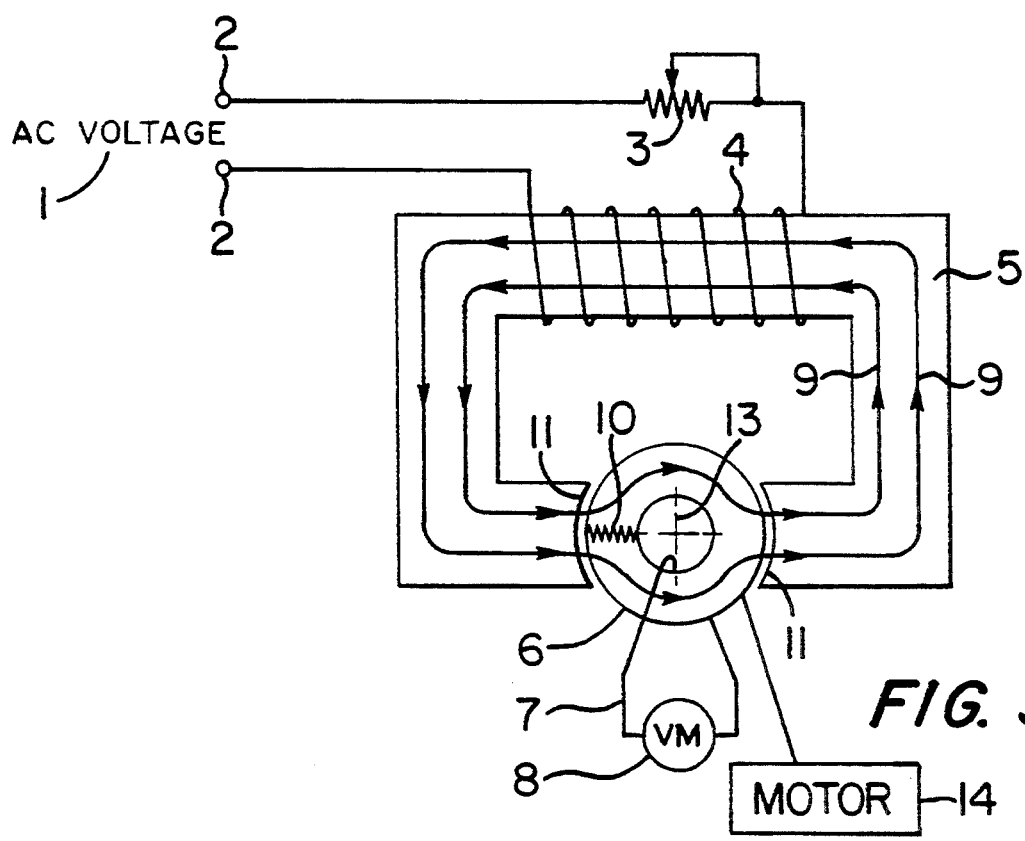
Figure 6:
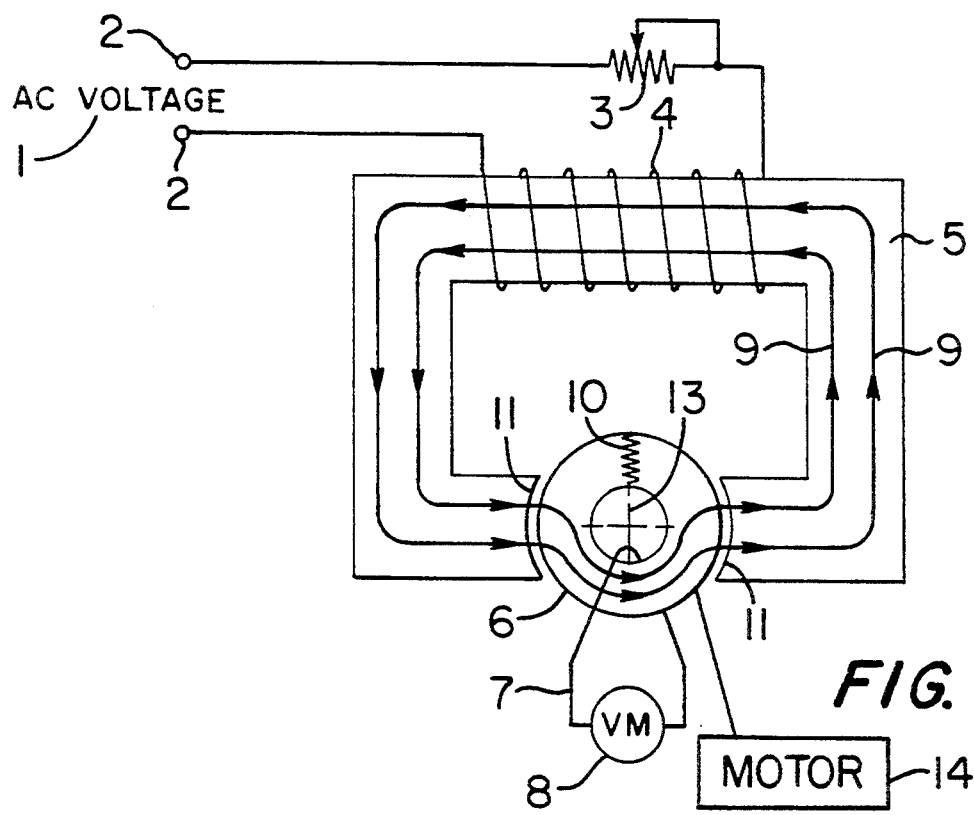

In FIG. 4, the source of flux consists of an electromagnet 5 resembling an interrupted rectangle with the magnetic core 6 located on one leg of the electromagnet 5. Pole faces 11 face the magnetic core in its plane, and flux 9 flows through the electromagnet and the magnetic core 6 under test in response to the current produced in coil 4 of the electromagnet 5. This current is determined by a source of AC Voltage i impressed upon terminals 2 and controlled by variable resistor 3 in series with the winding 4 of electromagnet 5. A search coil 7, which may consist of one or more turns, is located at a specific point on the magnetic core 6 under test, and the search coil 7 is connected to a sensitive volt meter 8 in order to obtain a reading of voltage in response to the flux 9 linked by search coil 7 in accordance with the transformer equation. The magnetic core under test is rotatable through 360° about axis 13. A motor 14 effects this rotation. In FIG. 4 is shown a good magnetic core without magnetic disturbance of any type, such that rotation of the core 6 about the axis 13 will not result in any change in the path of the flux 9 through the core. As a result, a certain value of voltage will be continuously recorded by volt meter 8 in response to this flux 9. FIG. 5 is the same fixture as shown in FIG. 4, except that the magnetic core 6 has a magnetic anomaly 10 located on the horizontal axis. Because of the location of this magnetic anomaly, the voltage recorded by volt meter 8 in response to the flux 9 linking search coil 7 will be exactly the same as the reading for a good core as shown in FIG. 4. FIG. 6 is the same as FIG. 5, but the magnetic core has been rotated 90' in a clockwise fashion such that magnetic anomaly 10 represents a low permeability path, and flux 9 will tend to travel in a path of higher permeability and away from the magnetic anomaly in the magnetic core under test. As a result, the voltage recorded by volt meter 8 in response to the flux 9 linked by search coil 7 will be much higher than the reading for FIGS. 4 or 5. Similarly, as the magnetic core is rotated about axis 13, magnetic anomaly 10 assumes different positions causing the reading of volt meter 8 to increase in value and have two peaks, at 90° and 270° respectively during rotation of the core, and two low readings, at 0° and 180° respectively. Thus, a core which is bad due to magnetic anomaly will indicate a variation in the reading of the volt meter, whereas a good core will maintain a steady and consistent reading as the core is rotated.

It's obvious that variations in the dimensions of the magnetic core that depart from symmetry, and in the location of the magnetic core within the text fixture itself that depart from a symmetrical condition can cause minor variations in the path of the flux 9 of even a good core, and fringing flux will have the same effect, so that a practical production fixture can expect to have some tolerance assigned to it to allow for the variation in the reading of volt meter 8. This can easily be determined by analysis of cores known to perform acceptably in the final application in comparison with cores which do not.

Should a core contain more than one magnetic anomaly, it will almost certainly exhibit very low total permeability and be rejected as a result of that type of test. In the event it is not, voltage readings from any of the fixtures described will be low and/or erratic, indicating a problem, even in the unlikely event that two anomalies occur exactly 180° apart.

Figure 7:
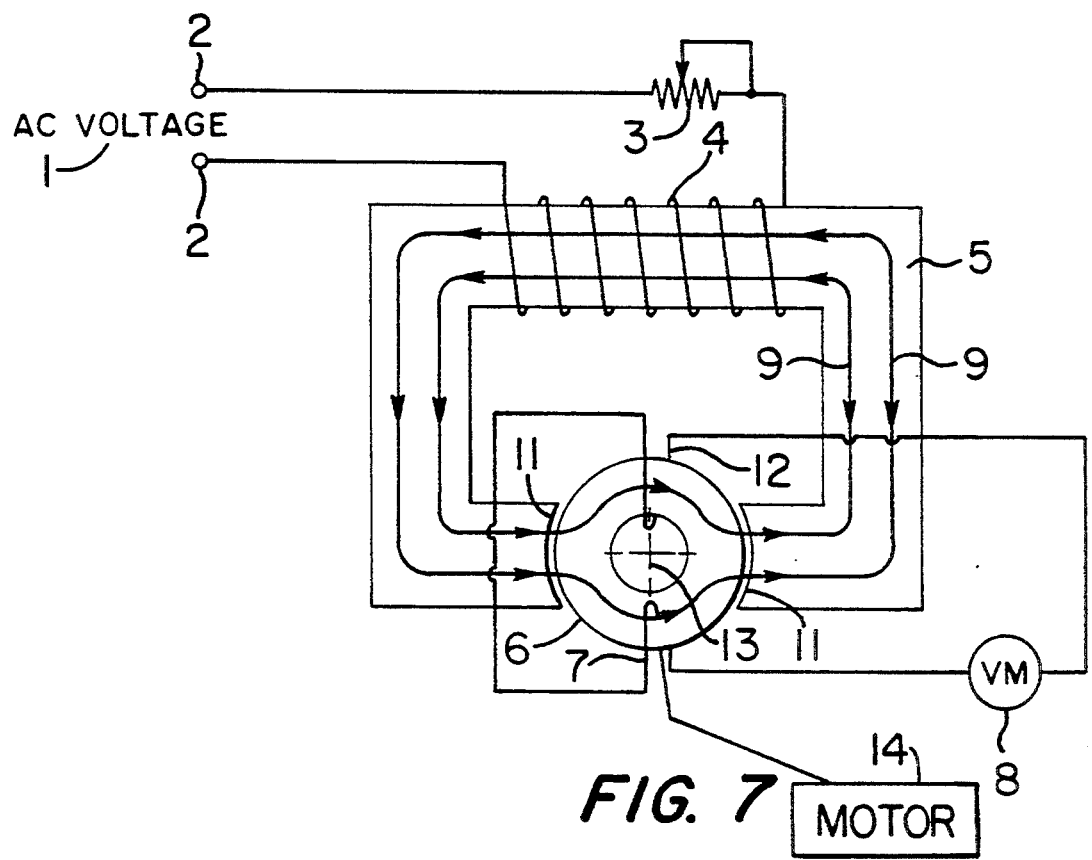
Figure 8:
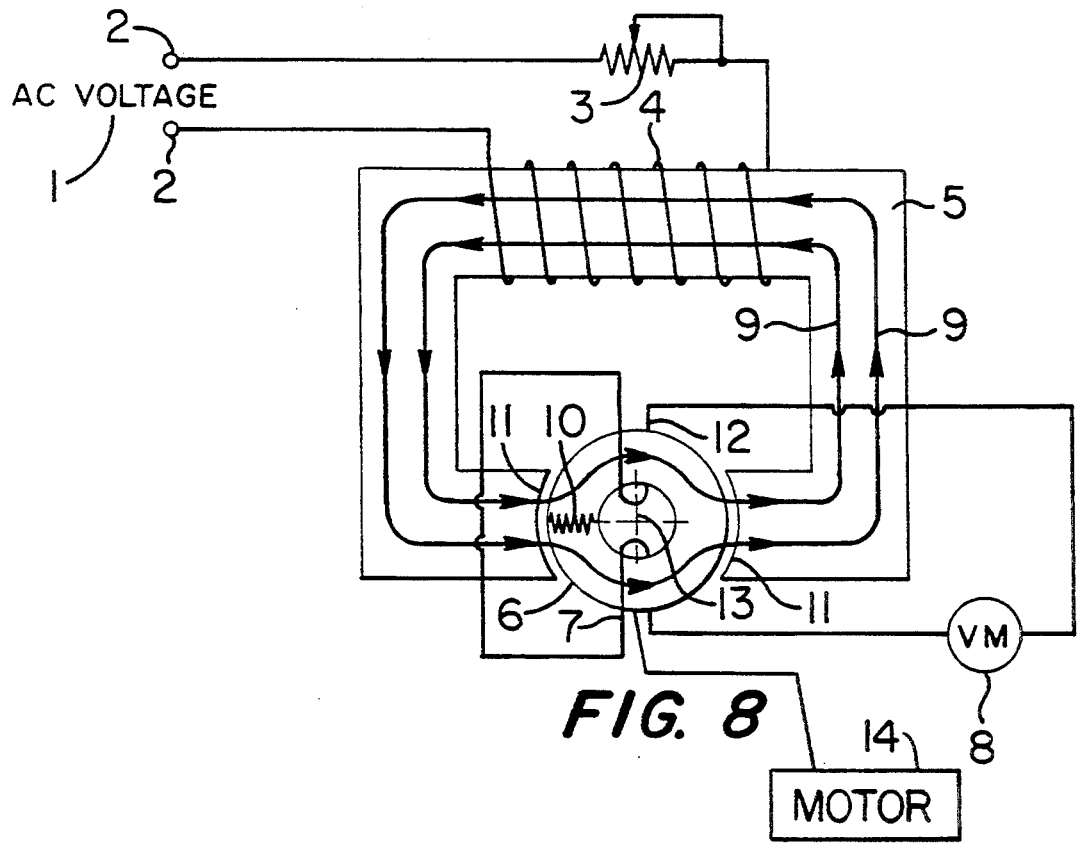
Figure 9:
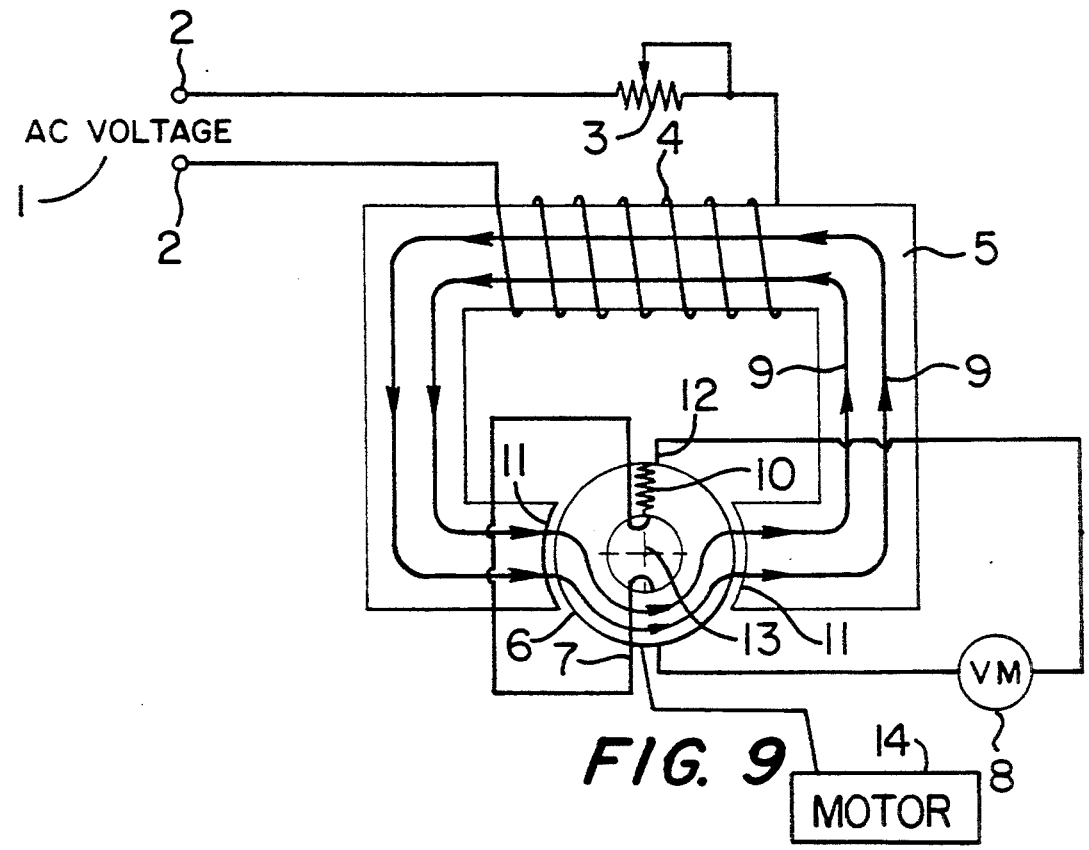

FIGS. 7 through 9 show a fixture similar to that of FIGS. 4 through 6, with the exception that two search coils in opposing relationship are employed at specific points located 180° apart along the plane of the magnetic core under test. The advantage of this scheme is that the voltage produced by search coil 7 opposes that produced by search coil 12, such that a good core 6 under test will produce essentially zero voltage in volt meter 8. Similarly, a core with a magnetic anomaly 10 located in the position shown in FIG. S will also produce zero voltage, whereas that core with its magnetic anomaly rotated 90° as shown in FIG. 9 will produce a positive voltage. In a similar fashion, the voltage will again be zero when the magnetic anomaly is at a position 180° removed from the position shown in FIG. 8, and again produce a maximum reading when the magnetic anomaly 10 is at a position located 270° from that shown in FIG. 8.

Figure 10:
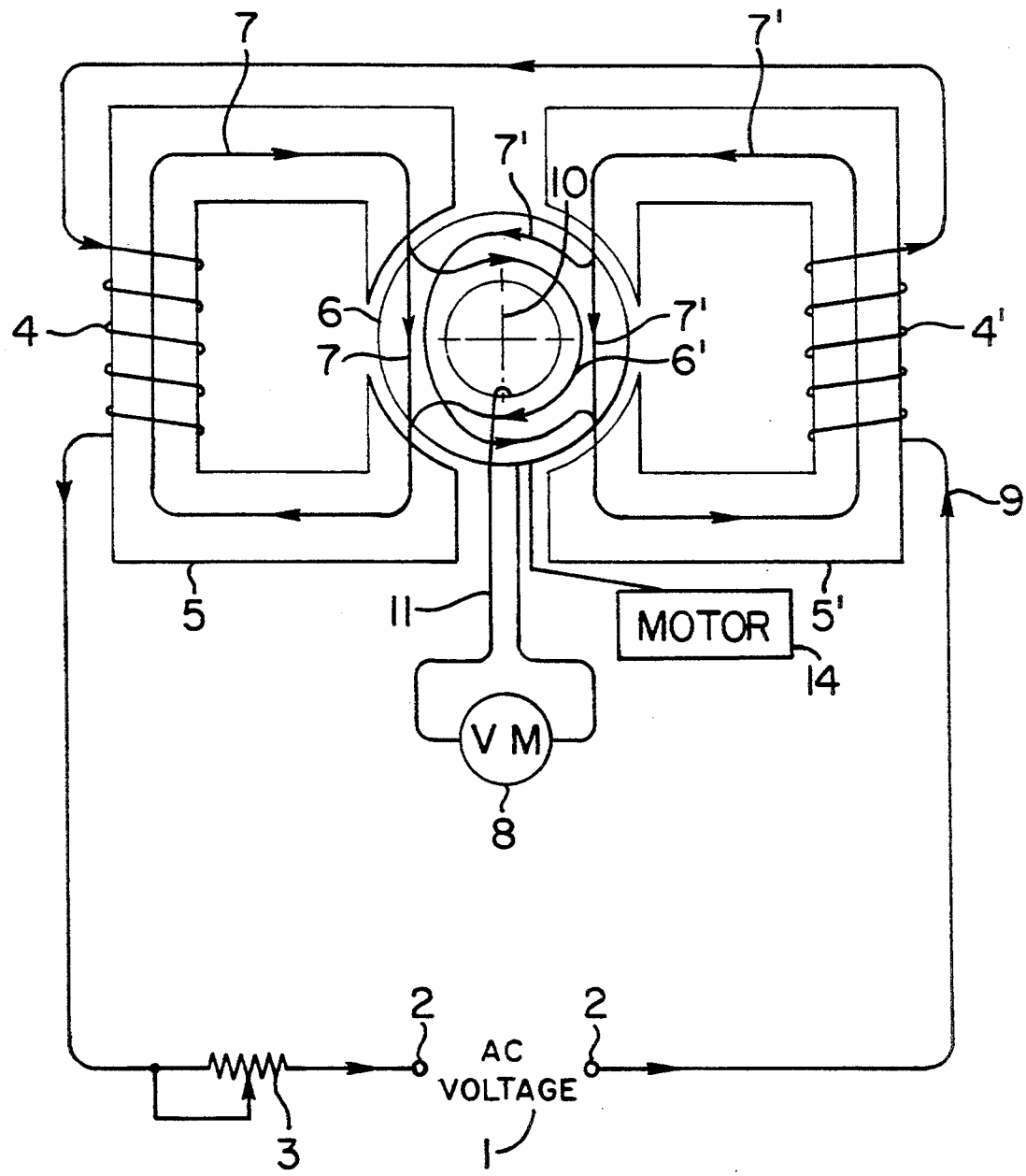
Figure 11:
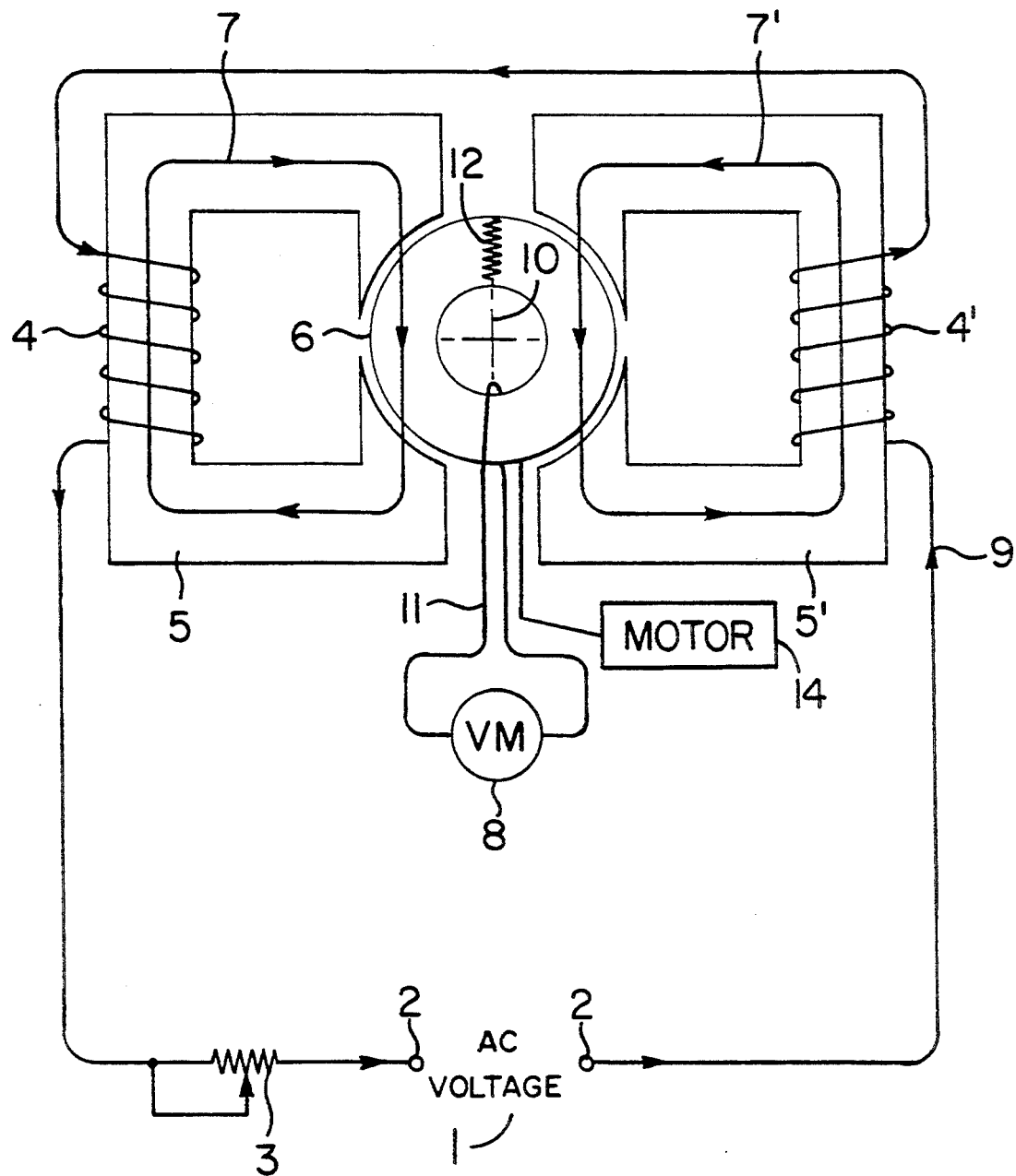
Figure 12:
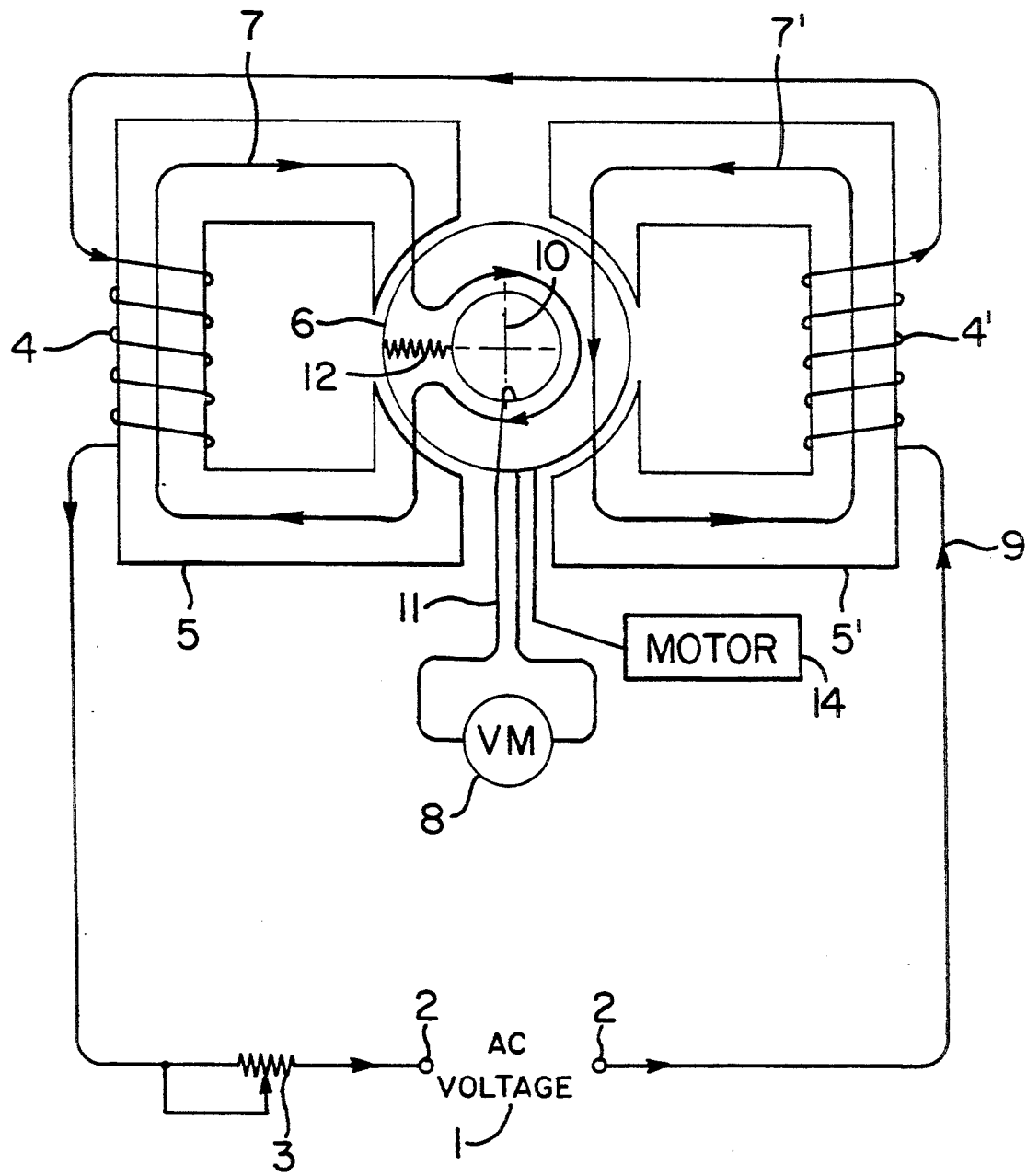

FIGS. 10 through 12 show a test fixture similar to that shown in FIG. 3 in which "bucking fluxes" are employed. In this fixture, electromagnets 5 and 5' consisting of interrupted rectangles with magnetic core 6 located at the point where the electromagnets are interrupted, in a symmetric fashion are free to rotate about axis 10. A source of AC voltage 1 is impressed upon terminals 2 and controlled by variable resistor 3 in order to produce a current 9 through the windings 4 and 4' of the electromagnets 5 and 5'. As a result of the winding configuration of coils 4 and 4', fluxes 7 and 7' flow toward each other through the magnetic core 6 under test, where these fluxes split or divide to take paths determined by the permeability of the relative paths in well-known means. Portions of flux 7 and 7' pass in opposing directions through the section of magnetic core 6 where search coil 11 is located and connected to volt meter 8. Since these fluxes are essentially equal, volt meter S has zero reading. FIG. 11 shows the same test fixture but with a magnetic core 6 with magnetic anomaly 12 located in the fixture. Again, it can be seen that volt meter 8 will have essentially zero voltage reading because fluxes 7 and 7' will not have any portions that flow through the core towards magnetic anomaly 12, and there will be essentially zero flux flowing through the area of search coil 11 and therefore zero voltage indicated on volt meter 8. FIG. 12 shows the magnetic anomaly rotated 90° in a counter-clockwise fashion such that flux 7 will choose a long path around the core under test, and all of flux 7 will be linked by search coil 11 connected to volt meter 8, giving a positive reading. In a similar fashion, as the magnetic core continues to rotate about axis 10, zero readings will occur at points 180° from that shown in FIG. 11, with maximums at 90° and 270° from the position shown in FIG. 11.

Figure 13:
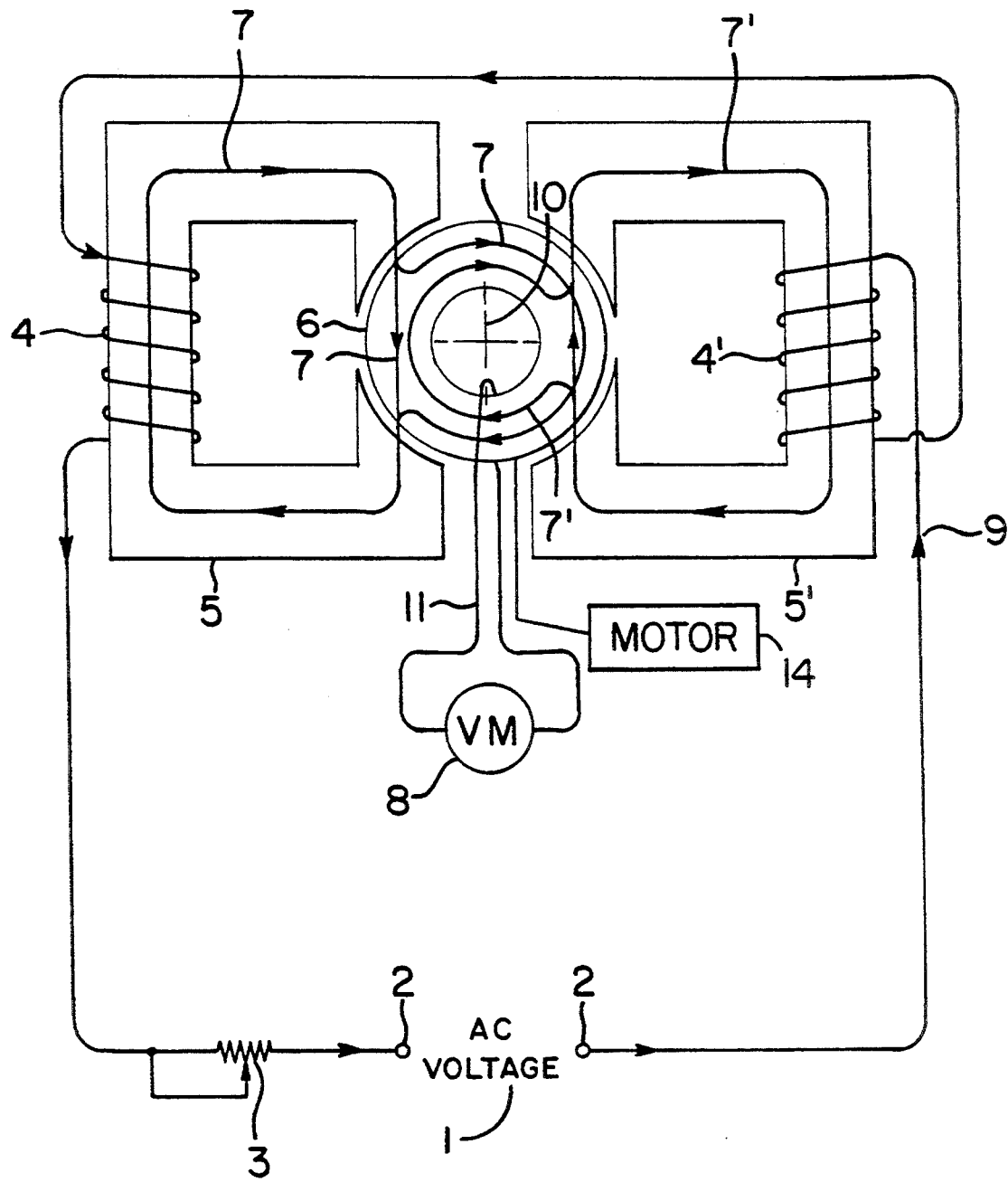
Figure 14:
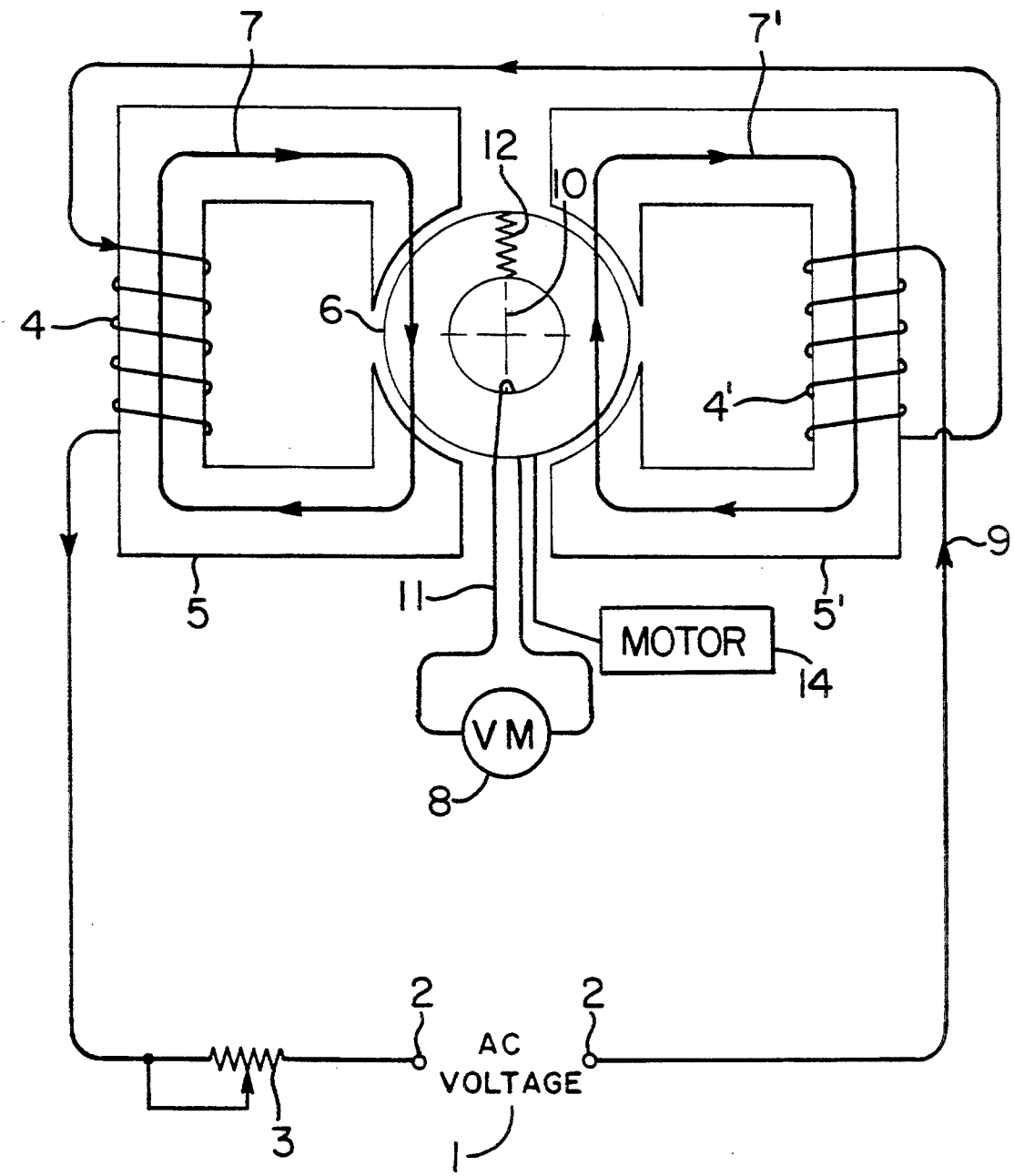
Figure 15:
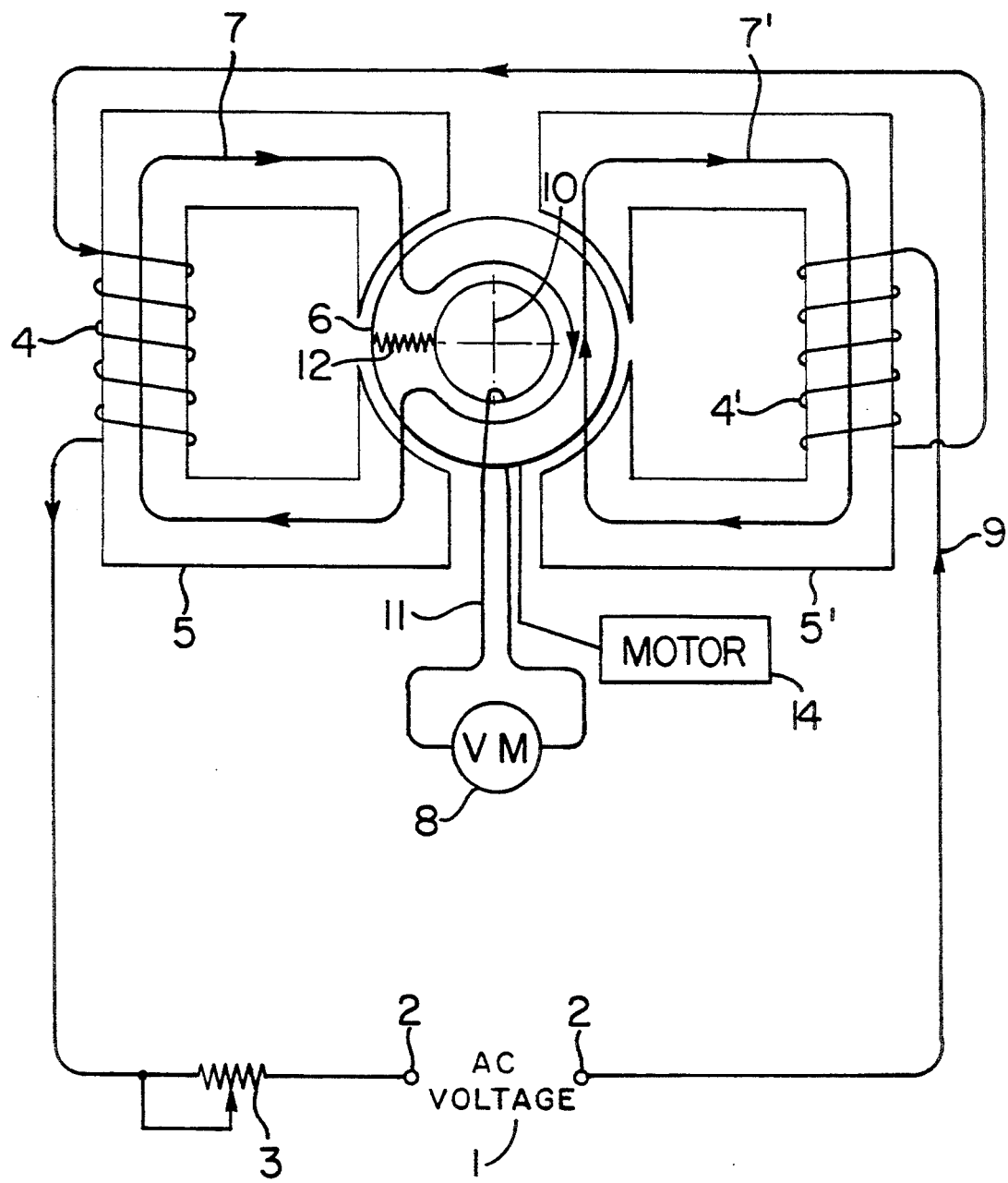

FIGS. 13 through 15 are essentially the same as shown in FIGS. 10 through 12, with the exception that electromagnet 4' has been rewired to produce flux in a direction that aids the flux produced by electromagnet coil 4. As can be seen in FIG. 13, search coil 11 links a significant portion of the flux 7 and 7' which is now in an aiding relationship, such that volt meter 8 will produce a high and unvarying voltage regardless of the rotation of a good core 6 about the axis 10 in this test fixture. In FIG. 14, a core with a magnetic anomaly 12 will produce essentially zero voltage because the flux 7 and 7' will choose to flow in a path of high permeability are away from a path interrupted by the low permeability region caused by magnetic anomaly 12. In FIG. 15, magnetic anomaly 12 has been rotated 90° in a counter-clockwise direction from that shown in FIG. 14, and flux 7 now chooses a path that links search coil 11 connected to volt meter 8, producing a value of voltage at a maximum that is one half the value of that produced by a good core in any position.

Again, as core 6 is rotated about axis 10, zero readings occur at 180° from the position shown in FIG. 14, while maximum readings, equal to one half of the reading given by a good core occur at positions 90° and 270° from that shown in FIG. 14.

FIGS. 4 through 15 serve to illustrate the various means by which the invention may be practiced, and it should be obvious that variations are possible. The use of multiple search coils, search coils connected to individual meters, the substitution of indicators or actuators for the meters, the use of amplifiers, and other forms of flux sources should be obvious.

Figure 16:
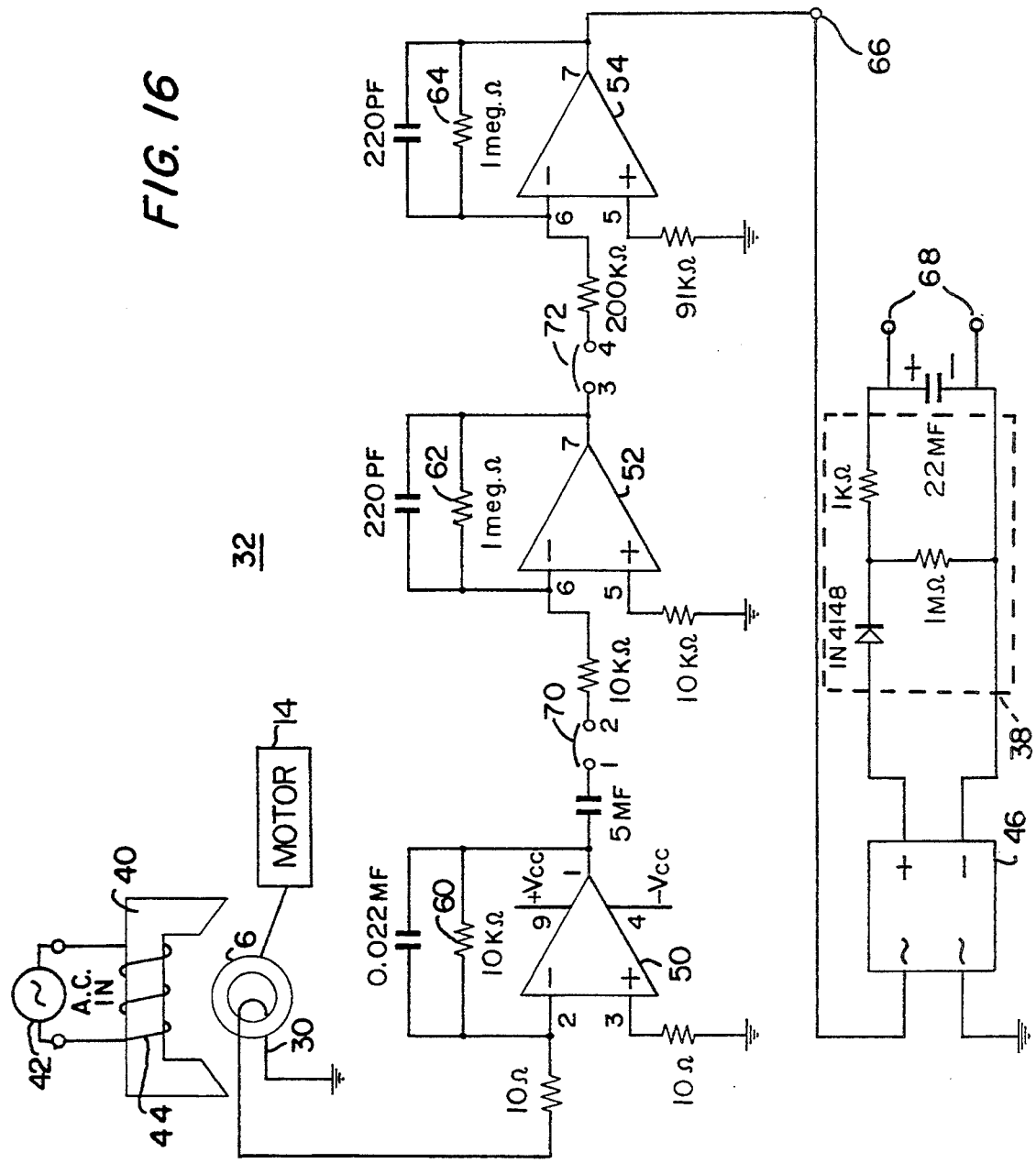
FIG. 16 is a schematic diagram of the apparatus utilized to evaluate the homogeneity or variation in permeability of a magnetic core.

Referring to FIG. 16, a schematic diagram of the amplifier 32 configuration used to evaluate the homogeneity or variation in permeability of a magnetic core is illustrated. As shown therein, a uniform magnetic field is created in the vicinity of the core under test by utilizing an excitation core comprising conventional E laminations 40 constructed of grain oriented silicon steel with the center leg clipped off and the ends of the two outer legs cut on a diagonal. The 60 Hz A-C source 42 is configured to deliver about 200 ma of current to the winding 44 about the excitation core 40. The spatial amplitude and direction of the AC magnetic field thus created closely approximates the actual field present in the vicinity of the differential transformer used in the ground fault circuit interrupter.

The AC voltage induced in the core as a result of the magnetic field is coupled via a pickup winding to a multi-stage AC voltage amplifier 32 and filter 38 consisting of a plurality of inverting amplifiers 50, 52 and 54 and low pass filters 38 to reduce high frequency noise. As configured, the multi-stage amplifier utilizes 3 stages. The first stage 50 has a gain of 1000, the second stage 52 has a gain of 100, and the third stage 54 has a gain of 5. Thus, the total gain of the amplifier is 500,000. Under certain conditions it may not be necessary to utilize the full gain of the amplifier 32. Accordingly, the overall gain of the amplifier 32 may be changed by decreasing the value of the feedback resistors or by utilizing the jumper wires 70, 72 to bypass an entire stage.

Ideally, for a homogeneous core there should be not variation in the permeability thereof and the output AC voltage, i.e., the amplified and filtered induced AC voltage, should remain constant as the core is rotated, manually or otherwise, 360° about its central axis. On the other hand, it has been found that non-homogeneous cores, i.e., ones with anomalies, exhibit at least one maximum and one minimum as they are rotated through 360°.

Thus, by observing the change in value of the amplified and filtered induced AC voltage at AC output terminal 66 as the core is rotated 360° about its axis an indication of the degree of homogeneity or non-homogeneity of the core is obtained. More specifically, by calculating the ratio of the maximum output AC voltage to the minimum output AC voltage an indication of the degree of homogeneity or non-homogeneity of the core is obtained. In the ideal situation of a perfectly homogeneous core this ratio would be 1. It has been found experimentally that for the cores utilized in the differential transformers employed in ground fault circuit interrupters this ratio should not exceed 1.5.

in some situations because of the high noise level and very small input signal it may be difficult to measure the output AC voltage, except with an averaging digital oscilloscope. Thus, in accordance with the present invention, and in order to permit use of a relatively inexpensive instrument, a conversion circuit, which includes a rectifying circuit 46 and a low pass filter 38, is connected to the output terminal 66 of the AC voltage amplifier. The conversion circuit further reduces the noise associated with the amplified and filtered induced AC voltage and converts same to a DC level. As in the situation described above, by observing the change in value of the DC level at the D.C. output terminals 68 as the core is rotated 360° about its axis, an indication of the degree of homogeneity or non-homogeneity of the core is obtained.

Figure 17:
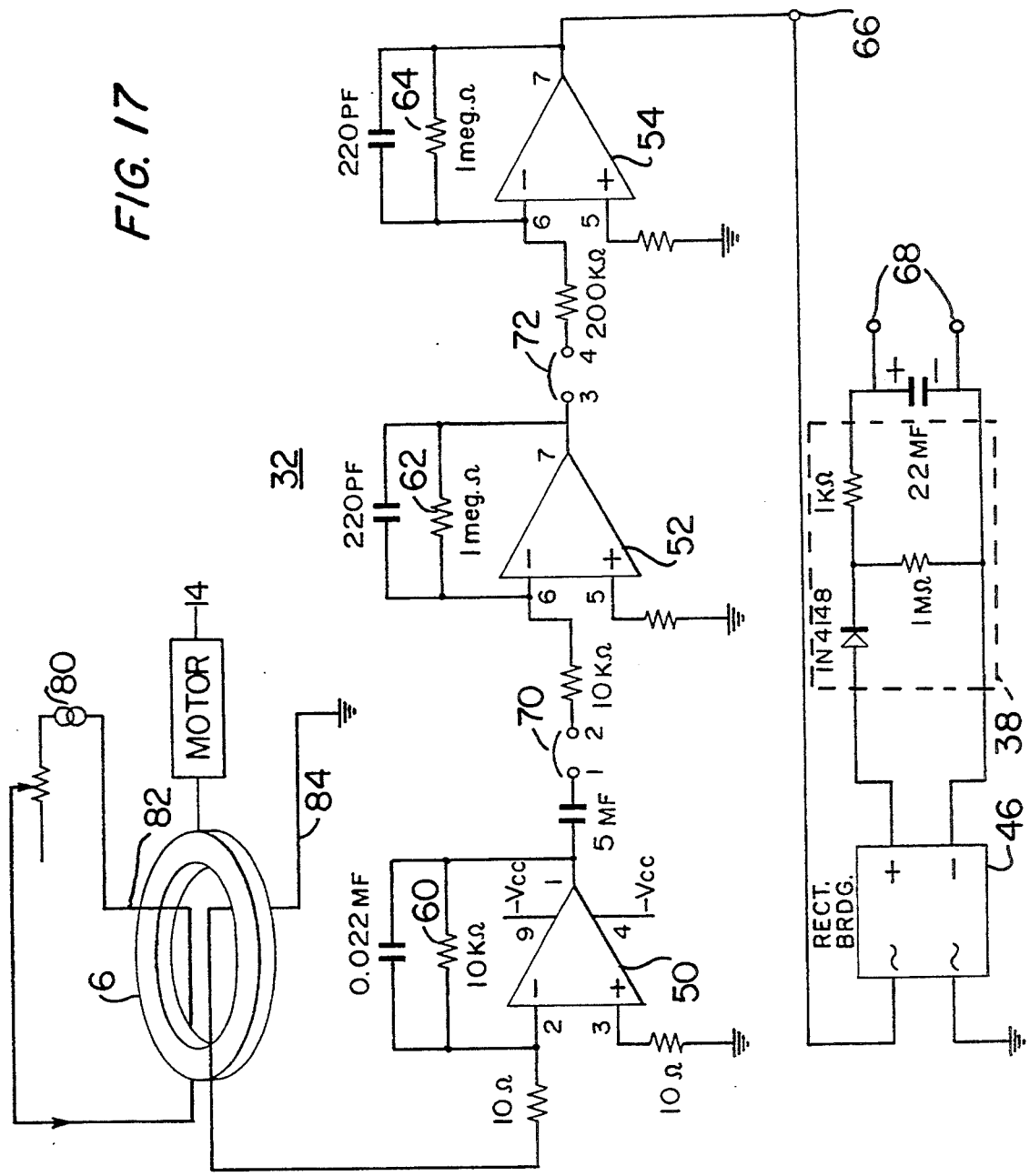
FIG. 17 is a schematic diagram of the apparatus utilized to measure the permeability of a magnetic core.

Referring now to FIG. 17, a schematic diagram of the amplifier configuration used to evaluate the permeability of a magnetic core 6 is illustrated. As shown therein, a 60 Hz current source 80 is utilized to provide an AC excitation current of 5 ma which is coupled via a primary winding 82 to the core. This level of excitation current conforms to the U.L. trip current requirement for ground fault circuit interrupter. The AC voltage induced in the core, 6 as a result of the excitation current applied thereto, is coupled via a secondary winding 84 to a multi-stage AC voltage amplifier and filter identical to the one depicted and discussed above in conjunction with FIG. 16. As discussed in more detail below, the value of the amplified and filtered induced AC voltage may be utilized in conjunction with predetermined and premeasured characteristics of the core 6 and the number of turns in the primary and secondary windings, 82, 84 respectively, to determine the value of the permeability of the core 6.

Again, because of the high noise level and very low input signal it may be difficult in some situations to measure the output AC voltage, except with an averaging digital oscilloscope. Thus, as was the situation described above, a conversion circuit identical to the one depicted and discussed in conjunction with FIG. 16 may be advantageously utilized to further reduce the noise associated with the amplified and filtered induced AC voltage and convert same to a DC level. As illustrated in the example below, the value of the De level is utilized in conjunction with predetermined and premeasured characteristics of the core, the number of turns in the primary and secondary windings, 82, 84 respectively, and the AC/DC slope characteristic of the AC voltage amplifier to determine the value of the permeability of the core 6. The AC/De slope characteristic of the AC voltage amplifier is determined by plotting the output peak to peak AC voltage versus the output DC voltage for different values of input excitation current.

The following example illustrates the steps to be followed to determine the value of the permeability of a typical core utilizing the apparatus illustrated in FIG. 17, including the conversion circuit.

CORE PERMEABILITY CALCULATIONS

1. Measured dimensions of a ring:
   A, Mean path length, L=3,296 cm
   B. Cross-sectional area of one ring, A=0,00562 cm$^2$
2. Magnetizing force (oersteds):

$$H = \frac{0.4 \times \times N \times I}{0.707 \times L}$$

Where:
   N—#of turns of the primary
   I—RMS current
   L—Mean path length
3. Flux density (gausses)

$$B = \frac{Vrms \times 10^8}{4.44 \times A \times n \times N \times F \times Av}$$

Where:
   V— rms output voltage which is calculated by the measured D.C. output voltage and the corresponding AC/DC.
   A=Cross-sectional area of one ring.
   n=#of rings
   F=Frequency
   N=# of turns on the secondary
   Av—amplifier gain
   Av—500,000 (input to the first stage)
   Av—500 (input to the second stage)
   AV—5 (input to the third stage)
4. Core Permeability=

$$\mu = \frac{B}{H}$$

Where;
   B=Flux density (gausses)
   H=Magnetizing force (oersteds)
5. Sample calculations of permeability Let us assume that the transformer has 5 rings and 5 ma rms current is applied to the primary. The secondary is connected to stage #1 (Av=500,000). The turns ratio is 1:1.

A. $H = \frac{0.4 \times \times N \times I}{0.707 \times L} = 0.002696$ $N = 1, I = 5$ ma(rms), $L = 3.296$ cm B. $B = \frac{Vrms \times 10^8}{4.44 \times A \times n \times N \times F \times Av} = 170$ -continued
$$V_{rms} = \frac{AC/DC \times DC(v) \times 0.707}{2}$$

Similarly, let us assume that the determined value of AC/DC =2.4 and that the measured output D.C. (v) −7.51 v.
Vrms—6.37 v
A=0.00562 cm²
n=5
N−1
F=60 Hz
Av=500,000

C. $\mu = \frac{B}{H}$ $$\mu = \frac{170}{0.002696} = 63056$$

It is to be understood that the embodiments of this invention which have been described and illustrated herein are by way of illustration and not of limitation, and that this invention may be practiced in a wide variety of other embodiments without departing materially from the spirit or scope of this invention, which is defined by the following claims.

What is claimed is:

1. Apparatus for evaluating the permeability of a toroidal magnetic core comprising:
   an electromagnet comprising an element of magnetic material and comprising a first winding having at least one turn encircling at least a portion of the periphery thereof;
   AC current source means directly coupled to said first winding for causing a predetermined flux field to extend through said magnetic material of said electromagnet to said core positioned adjacent said magnetic material of said electromagnet;
   Means for rotating said core adjacent said magnetic material of said electromagnet and subjecting said core to the flux field of said electromagnet;
   a second winding having at least one turn encircling at least a portion of the periphery of said core;
   AC voltage amplifying means including means for allowing the passing of AC voltage induced in said second winding as said core is rotated through said second winding, having a frequency below a predetermined frequency, operatively coupled to said second winding on said core for amplifying and filtering the resulting AC voltage induced in said second winding by said flux field of said electromagnet, the change in value of said amplified and filtered induced AC voltage as said core is rotated 360 degrees about its axis being indicative of the variation in permeability of said core.

2. Apparatus for evaluating the permeability of a toroidal magnetic core comprising:
   an electromagnet comprising an element of magnetic material and comprising a first winding having at least one turn encircling at least a portion of the periphery thereof;
   AC current source means directly coupled to said first winding for causing a predetermined flux field to extend through said magnetic material of said electromagnet to said core positioned adjacent said magnetic material of said electromagnet;
   means for rotating said core adjacent said electromagnet and subjecting said core to the flux field of said electromagnet;
   a second winding having at least one turn encircling at least a portion of the periphery of said core;
   AC voltage amplifying means including means for allowing the passing of AC voltage induced in said second winding as said core is rotated through said second winding, having a frequency below a predetermined frequency, operatively coupled to said second winding on said core for amplifying and filtering the resulting AC voltage induced in said core by flux field of said electromagnet; and
   conversion means including rectifying means and low pass filtering means operatively connected to the output of said AC voltage amplifying means for further reducing the noise associated with the amplified and filtered induced AC voltage and converting same to a DC voltage level, the change in value of said DC voltage level as said core is rotated 360 degrees about its axis indicative of the variation in the permeability of said core.

3. The apparatus of claim 1 wherein said AC voltage amplifying means comprises a plurality of stages connected in series with each other, each of said stages comprising an operational amplifier, an input resistor connected in series with a negative input terminal of said operational amplifier, a feedback resistor connected between the output of said operational amplifier and said negative input terminal, a capacitor connected in parallel with said feedback resistor, and a ground resistor connected between a positive input terminal of said operational amplifier and ground.

4. The apparatus of claim 2 wherein said AC voltage amplifying means comprises a plurality of stages connected in series with each other, each of said stages comprising an operational amplifier, an input resistor connected in series with a negative input terminal of said operational amplifier, a feedback resistor connected between the output of said operational amplifier and said negative input terminal, a capacitor connected in parallel with said feedback resistor, and a ground resistor connected between a positive input terminal of said operational amplifier and ground.

5. The apparatus of claim 2 wherein said conversion means including rectifier means and low pass filtering means comprises a rectifier bridge circuit connected to an output of said AC voltage amplifying means, a diode having its anode connected to a positive output terminal of said rectifier bridge circuit, a first resistor connected to the cathode of said diode and to a negative output terminal of said rectifier bridge circuit, a second resistor connected to said cathode of said diode, and a capacitor connected to said second resistor and to said negative output terminal of said rectifier bridge circuit.

6. The apparatus of claim 5 wherein said AC voltage amplifying means comprises a plurality of stages connected in series with each other, each of said stages comprising an operational amplifier, an input resistor connected in series with a negative input terminal of said operational amplifier, a feedback resistor connected between the output of said operational amplifier and said negative input terminal, a capacitor connected in parallel with said feedback resistor, and a ground resistor connected between a positive input terminal of said operational amplifier and ground.

7. A method for evaluating the permeability of a toroidal magnetic core comprising the steps of:

applying a predetermined excitation current to an electromagnet comprising an element of magnetic material and a first winding, having at least one turn encircling the periphery thereof, said excitation current being applied to said first winding to cause a predetermined flux to extend through said magnetic material;

rotating said core adjacent said magnetic material of said electromagnet and subjecting said core to the flux of said electromagnet;

detecting the AC Voltage induced in a second winding having at least one turn encircling said core as said core is rotated through said second winding;

amplifying and filtering the detected AC voltage induced in said second winding such that only AC voltage having a frequency below a predetermined frequency is available at the output of said amplifying and filtering apparatus; and observing the change in value of said amplified induced AC voltage as said core is rotated 360 degrees about its axis, the change in value of said amplified and filtered AC induced voltage being indicative of the variation in permeability of said core.

8. A method for evaluating the permeability of a toroidal magnetic core comprising the steps of:

applying a predetermined excitation current to an electromagnet comprising an element of magnetic material and a first winding having at least one turn encircling the periphery thereof, said excitation current being applied to said first winding to cause a predetermined flux to extend through said magnetic material;

rotating said core adjacent said magnetic material of said electromagnet and subjecting said core to the flux of said electromagnet;

detecting the AC voltage induced in a second winding having at least one turn encircling said core as said core is rotated through said second winding;

amplifying and filtering the detected AC voltage induced in said second winding such that only AC voltage having a frequency below a predetermined frequency is available at the output of said amplifying and filtering apparatus;

further reducing the noise associated with the amplified and filtered induced AC voltage by passing said AC voltage through a low pass filter and converting the output of said low pass filter to a D.C. voltage level; and observing the change in value of said D.C. voltage level.

9. The method of claim 7 wherein said amplifying and filtering comprises applying said resulting AC voltage to the input of an amplifier circuit comprising a plurality of stages connected in series with each other, each of said stages comprising an operational amplifier, an input resistor connected in series with a negative input terminal of said operational amplifier, a feedback resistor connected between the output of said operational amplifier and said negative input terminal, a capacitor connected in parallel with said feedback resistor, and a ground resistor connected between a positive input terminal of said operational amplified and ground.

10. The method of claim 9 further comprising using jumper wires to interconnect said stages of said amplifier circuit such that selected said stages can be bypassed by reconnecting said jumper wires.

11. The method of claim 8 wherein said amplifying and filtering comprises applying said resulting AC voltage to the input of an amplifier circuit comprising a plurality of stages connected in series with each other, each of said stages comprising an operational amplifier, an input resistor connected in series with a negative input terminal of said operational amplifier, .a feedback resistor connected between the output of said operational amplifier and said negative input terminal, a capacitor connected in parallel with said feedback resistor, and a ground resistor connected between a positive input terminal of said operational amplifier and ground.

12. The method of claim 11 further comprising using jumper wires to interconnect said stages of said amplifier circuit such that selected said stages can be bypassed by reconnecting said jumper wires.

13. The method of claim 8 wherein said reducing the noise associated with the amplified and filtered induced AC voltage and converting said to a DC level comprises applying said amplified and filtered induced AC voltage to the input of a circuit comprising a rectifier bridge, a diode having its anode connected to a positive output terminal of said rectifier bridge, a first resistor connected to the cathode of said diode and to a negative output terminal of said rectifier bridge, a second resistor connected to said cathode of said diode, and a capacitor connected to said second resistor and to said negative output of said rectifier bridge.

14. The method of claim 13 wherein said amplifying and filtering comprises applying said resulting AC voltage to the input of an amplifier circuit comprising a plurality of stages connected in series with each other, each of said stages comprising an operational amplifier, an input resistor connected in series with a negative input terminal of said operational amplifier, a feedback resistor connected between the output of said operational amplifier and said negative input terminal, a capacitor connected in parallel with said feedback resistor, and a ground resistor connected between a positive input terminal of said operational amplifier and ground.

15. The method of claim 13 further comprising using jumper wires to interconnect said stages of said amplifier circuit such that selected said stages can be bypassed by reconnecting said jumper wires.

16. The method of claim 14 further comprising using jumper wires to interconnect said stages of said amplifier circuit such that selected said stages can be bypassed by reconnecting said jumper wires.

* * * * *